United States Patent [19]

Prizzi, Jr.

[11] Patent Number: 5,514,141

[45] Date of Patent: May 7, 1996

[54] SMALL JOINT REAMER

[75] Inventor: John Prizzi, Jr., West Milford, N.J.

[73] Assignee: Howmedica, Inc., New York, N.Y.

[21] Appl. No.: 249,579

[22] Filed: May 26, 1994

Related U.S. Application Data

[63] Continuation of Ser. No. 964,984, Nov. 18, 1992, abandoned.

[51] Int. Cl.$^6$ .................................................. A61B 17/56
[52] U.S. Cl. ............................ 606/80; 606/79; 606/180
[58] Field of Search ........................... 606/167, 170,
606/171, 180, 79, 80, 81, 84, 85; 408/223,
224, 229, 211, 703–708, 712, 713, 227;
407/54, 55, 56, 58, 60–62; 433/102, 165,
166

[56] References Cited

U.S. PATENT DOCUMENTS

| | | | |
|---|---|---|---|
| 1,438,168 | 12/1922 | Brown | 433/165 |
| 1,636,577 | 7/1927 | Schuller | 433/165 |
| 1,827,511 | 10/1931 | Evans | 433/165 |
| 1,927,463 | 9/1933 | McIntosh . | |
| 3,337,936 | 8/1967 | Curry | 406/54 |
| 3,892,117 | 7/1975 | Nelson | 433/165 |
| 4,116,200 | 9/1978 | Braun et al. . | |
| 4,246,895 | 1/1981 | Rehder . | |
| 4,284,080 | 8/1981 | Rehder . | |
| 4,472,094 | 9/1984 | Anderson | 408/203.5 |
| 4,573,838 | 3/1986 | Omi et al. | 408/204 |
| 4,795,289 | 1/1989 | Potemkin | 408/80 |
| 4,798,503 | 1/1989 | Huju . | |
| 4,997,322 | 5/1991 | Wells et al. . | |
| 5,004,383 | 6/1991 | Elliott, Jr. . | |
| 5,108,405 | 4/1992 | Mikhail et al. | 606/96 |
| 5,122,134 | 6/1992 | Borzone et al. | 606/80 |
| 5,190,548 | 3/1993 | Davis | 606/80 |

FOREIGN PATENT DOCUMENTS

| | | | |
|---|---|---|---|
| 182283 | 6/1953 | Australia | 407/54 |
| 2304322 | 10/1976 | France . | |
| 2554709 | 5/1985 | France . | |
| 2633509 | 1/1990 | France . | |
| 2543723 | 4/1977 | Switzerland . | |
| 2748452 | 5/1979 | Switzerland . | |
| 2834297 | 2/1980 | Switzerland . | |
| 1277769 | 6/1972 | United Kingdom . | |

*Primary Examiner*—Stephen C. Pellegrino
*Assistant Examiner*—Guy V. Tucker
*Attorney, Agent, or Firm*—Pennie & Edmonds

[57] ABSTRACT

A reamer designed to create convex, curved shapes on small bones. The reamer comprises a body with a center bore throughout, and a concave head with at least three flutes. The flutes extend from the center of the head outward, being unconnected to each other in any way except at the center of the head portion. Each flute has an outer curved surface, which together form the partially hemispherical outer surface of the head. The inner curved surface is angled to facilitate rapid clearing of bone chips from the work surface. The distal end of each flute has a flat end surface, which is sufficiently large to prevent the flutes from breaking. Each flute also has two side surfaces, a cutting surface and a non-cutting surface. The small joint reamer according to the invention allows bone chips to be cleared easily during operation. This prevents overheating of the bone surface, which can cause necrosis of the bone, preventing proper healing of the patient.

16 Claims, 1 Drawing Sheet

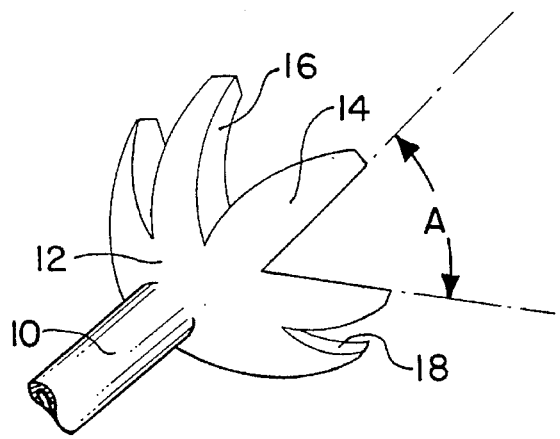
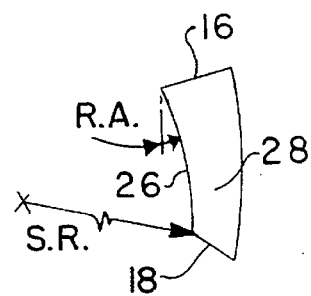
FIG. 5
FIG. 1
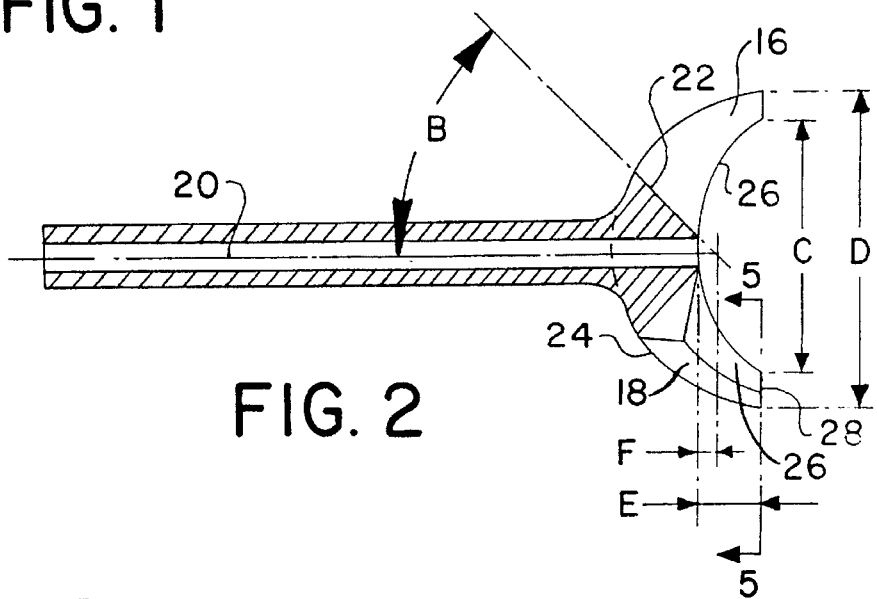
FIG. 2
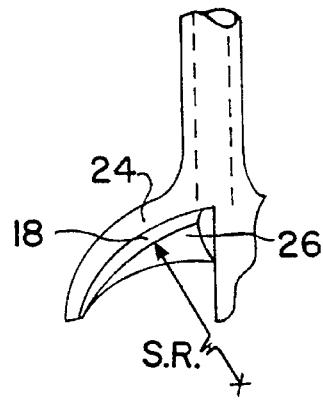
FIG. 3
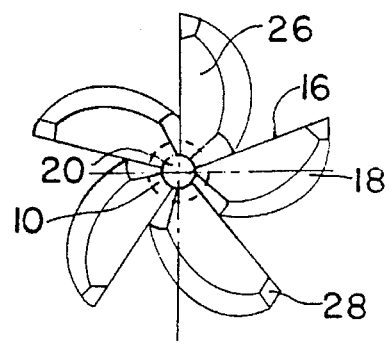
FIG. 4

5,514,141

SMALL JOINT REAMER

This is a continuation, of application Ser. No. 07/964,985, filed Nov. 18, 1992, now abandoned.

BACKGROUND OF THE INVENTION

This invention relates to shaping tools, and more particularly to concave reamers used on small bones to make convex shapes on small bone ends in procedures for fusing joints.

Making a convex surface through the use of a tool is generally disclosed in prior art. U.S. Pat. Nos. 1,927,463 to Mcintosh, 4,798,503 to Huju, 4,997,322 to Wells, and 5,004,383 to Elliot disclose cutting tools that produce convex surfaces. U.S. Pat. No. 4,997,322 discloses a reamer for removing spot welds during automotive body repairs. U.S. Pat. No. 4,798,503 discloses a tool for forming tenons (conical shapes) onto the end of wood posts that is used with a hand drill.

The prior art includes tools used for shaping convex surfaces onto bone. For example British Patent No. 1,277,769 to Charnley discloses two tools, a concave and a convex, for use in hip joint surgery. The concave tool is a solid concave structure with cutting teeth along the inner surface for cutting the bone surface. U.S. Pat. No. 4,246,895 to Rehder discloses an apparatus for producing a conical, outwardly tapering surface on a bone, specifically the femur head of the hip joint.

French Patent Nos. 2,304,322 and 2,554,709 disclose tools for making convex surfaces on bone. German Patent Nos. DT 2,834,297 and DE 2,748,452 show milling cutters that create a hemispherical contour on a femoral bone prior to insertion in an acetabular prosthesis.

The prior art concave reamers for use on bones have been found deficient for use in fusing the joints of small bones in particular. The prior art reamers generally have a concave shape containing cutting blades along the inner surface. During operation, such reamers trap heat due to the contact with the bone surface and allow the accumulation of bone chips between the work surface and the reamer.

Some of the prior art reamers have attempted to solve this problem by having holes or slots within the concave head of the reamer to allow bone chips to be cleared and air to circulate to cool the bone surface. This design has proved inadequate, however, because bone chips can clog the holes of the reamer, and cause the bone surface to overheat. Bone is a living substance, which if overheated will die, preventing the healing process necessary for a successful fusing operation. The possible necrosis of the bone is especially detrimental in an operation to fuse joints, because the tissue must remain live to heal properly.

Another disadvantage of many of the prior art tools is that they form conical surfaces through the use of straight blades, such as U.S. Pat. No. 4,798,503 to Huju. It is, however, desirable to provide the bone with a spherical surface for the best results in a joint fusing operation.

Also, prior art tools that are designed to form partial spherical surfaces are often complicated to manufacture, and therefore expensive. For example, English Pat. No. 1,277,769 requires that cutting teeth be provided over a substantial part of the inner curved surface of the concave tool. This piece would be difficult and expensive to manufacture, especially in sizes small enough for use on small bones in the hands and feet.

SUMMARY OF THE INVENTION

It is an object of the present invention to satisfy the above-stated needs by providing a bone reamer that has a unique design to allow bone chips to be cleared easily, preventing the overheating of the bone surface. Another object of the present invention is to create a convex surface on a bone that is curved and approximately spherical, to be connected with a another bone that has been shaped into a concave surface. It is also an object of the present invention to provide a reamer that satisfies the above objects and also can be manufactured easily and inexpensively.

The reamer of the present invention has an open design, consisting of a plurality of flutes which are unconnected at their distal ends. This design creates large amounts of open space to clear bone chips and for air to circulate to cool the bone surface. The unique design of the reamer prevents necrosis of the bone surface.

The concave surface of the head of the reamer cuts a convex surface into a bone that is approximately spherical. This design allows the bone to be matched with another bone that has been cut with a convex reamer with an approximately spherical shape as well, the connection between the bones thus having a wide range realignment possibilities. The concave/convex union allows corrections in rotation, planer levels and angularity, giving bone the appropriate position for fusion.

A further object of the invention is to provide a reamer at a reasonable cost. The reamer of the present invention is relatively simple to manufacture due to its open structure, which can be cut from a single piece of metal. One embodiment of the present invention comprises a head of five flutes. This embodiment requires a minimum of machine set-ups to manufacture, and therefore can be made easily and inexpensively.

In general, these and other objects are achieved by a reamer comprising a body and a fluted head portion. The entire reamer has a central bore to allow a guide wire to be inserted into the bone surface to guide the reamer. The head portion of the reamer is concave in shape. The head comprises at least three flutes which extend from the center of the head portion outward.

Each flute has a cutting surface, which has an edge that engages and cuts the bone surface, and a non-cutting surface. The flutes are arranged so that the cutting surface of one flute is adjacent to a non-cutting surface of the adjacent flute. Each flute also has an outer curved surface, which forms the partially hemispherical shape of the head. Each flute also has an inner curved surface, which is slanted to facilitate the rapid clearing of bone chips generated by the cutting surface coming into contact with the bone.

BRIEF DESCRIPTION OF THE DRAWINGS

FIG. 1 is a perspective view of the outer curved surface and tubular body of the reamer of the present invention;

FIG. 2 is a cross-sectional view of the reamer;

FIG. 3 is a side view of the head of the reamer;

FIG. 4 is an end view of the head of the reamer; and

FIG. 5 is an end view of a single flute as viewed along the line 5—5 of FIG. 4.

DETAILED DESCRIPTION OF THE PREFERRED EMBODIMENTS

Referring first to FIG. 1, a preferred embodiment of the invention is seen to include body 10 of the reamer and head 12 of the reamer, which comprises a plurality of flutes 14, extending from the center of the head outward, and being unconnected at their distal ends. Each flute 14 has two side surfaces: a side cutting surface 16 and a side non-cutting surface 18. The angle A between the side cutting surface 16 and the adjacent side non-cutting surface 18 is between about 45°–65°. Preferably this angle will be between about 50°–60°, and most preferably about 55°. Too small of an angle reduces the amount of space for bone chips to clear and increases the risk of overheating the bone. Too large of an angle reduces the thickness of the flutes, resulting in a weaker reamer.

Referring to FIG. 2, a cross-sectional view of the entire reamer illustrates central bore 20 throughout the body and head of the reamer, as well as the concave shape of the head of the reamer. FIG. 2 also illustrates the angle B between line 22 formed at the juncture of two adjacent flutes 14 at their base, and the central axis of the reamer. Angle B is generally between about 35°–55°. Preferably this angle is between about 40°–50°, and most preferably about 45°. As with angle A, changes in angle B result in compromises between strength and performance of the reamer. Reducing angle B weakens the flutes and therefore the reamer by reducing the material in the central portion of head 12. Increasing this angle inhibits the rapid clearing of bone chips from the work surface.

FIG. 3 is a view of an individual flute 14 of the reamer, showing outer curved surface 24 and inner curved surface 26, as well as side non-cutting surface 18. The edge between non-cutting surface 18 and inner curved surface 26 falls along spherical radius S.R. The length of spherical radius S.R. defines the relief angle (R.A. shown in FIG. 5) of the flute. The appropriate relief angle for a particular size reamer can be determined by a person of ordinary skill in the art based on the disclosure herein.

FIG. 4 illustrates the flutes in detail, showing the inner curved surface 26, the side cutting surface 16, the side non-cutting surface 18, and the center bore 20 of body 10. In addition, each flute has at its distal end a flat end surface 28 which lies in the plane of FIG. 4. Each flute is at least approximately equally spaced. Thus, in the illustrated embodiment with five flutes, the angle between two side cutting surfaces of two adjacent flutes is approximately 72°.

There are certain aspects of the design that are variable characteristics that can be changed for specific applications. The number of flutes is such a characteristic. The number of flutes should be sufficient to cut a smooth, clean surface into the bone, but not so numerous that the space between the flutes becomes smaller, reducing the ability of the reamer to clear bone chips and prevent overheating of the bone. For smaller reamers, three flutes can be used, but for the average sizes, five flutes are used with excellent results. A reamer with five flutes is also easy to manufacture, requiring a minimum of machine set-ups.

Another variable dimension of the reamer is the size of the head of the reamer. The inner diameter C and outer diameter D of head 12 can be made smaller for smaller bones, such as in joints in the hand or of a child, and larger for larger bones in the foot. The inner diameter is the same diameter of the surface that will be cut into the bone surface, and should be determined according to the size of the bone. The outer diameter is preferably about 0.1 inches greater than the inner diameter, to provide flutes of sufficient strength. Changing the size of the head will also change the distances E and F. Distance E is the distance from inner surface 26 at the center of the reamer to end surface 28, measured along the central axis. Distance E determines the depth of the cut made by the reamer. Distance F is the distance from inner surface 26 at the center of the reamer to the vertex of angle B. This distance defines the thickness of the head.

An example of an embodiment of the reamer according to the invention as described above is as follows: To create a spherical surface on a bone with a diameter of 14 millimeters or 0.551 inches, the inner diameter C is 0.551 inches and the outer diameter D is approximately 0.650 inches. Distance E is approximately 0.15 inches and distance F is approximately 0.033 inches. Five flutes provides good results in this size. Therefore, the angle between the cutting surfaces of any two adjacent flutes is about 72°. The angle A between the side cutting surface of a flute and the adjacent side non-cutting surface of the adjacent flute is preferably approximately 55° and the angle B between the central axis and line 22 formed between each flute is preferably approximately 45°, as discussed above. The spherical radius S.R. for a reamer of this size according to the invention is preferably about 0.38 inches. This design results in flutes that are thick enough, as evidenced by the size of the flat end surface at the distal end of each flute, to prevent the flutes from breaking during use.

Based on the example provided, a person of ordinary skill in the art will be able to construct a reamer of any desired size in accordance with the invention described herein.

In alternative embodiments of the invention, the variables discussed above can be altered for different needs. For example, for use on a small bone, a 10 millimeter reamer could be used to create a curved, convex surface having a diameter C of 10 millimeters. For this application, a reamer with three flutes could be designed according to the invention to provide a sufficient amount of space for bone chips to clear. In this embodiment the angle between the cutting surfaces of each flute would be 120° degrees, however, angles A and B preferably would remain at about 55° and 45°, respectively. It has been found that these angles should remain approximately the same regardless of the other dimensions of the reamer.

When the reamer is used, it is attached to a drill to supply rotation of the reamer. A wire is inserted through the central bore into the center of the bone surface where the convex surface is desired. The reamer is rotated so that a perspective view of the outer curved surface would observe the flutes moving in a clockwise direction when the flutes are designed as shown in the drawings. The bone chips produced by the cutting action fall away from the work surface through the spaces between the flutes, and can not become trapped between the work surface and the reamer. The work surface thus remains cool, reducing or preventing necrosis of the bone.

What is claimed is:

1. A bone reamer, comprising:

an elongated body having first and second ends and defining a central longitudinal axis; and a head at the second end of the body, comprising at least three separate cutting flutes with first and second ends, said flutes joined at their first ends to form said head and extending radially and longitudinally outward therefrom with the second ends unconnected and spaced at least approximately equally from adjacent flutes, each said flute having an outer surface, a concave inner surface extending from the first end to the second end, a side cutting surface, an opposite side non-cutting surface and an end surface at the second unconnected end of the flute, the curved inner surface and the side cutting surface defining a curved cutting edge which extends radially and longitudinally from the first end of the flute to the second unconnected end, the cutting edge of said flutes together defining an inner concave, approximately semi-spherical surface upon rotation around said central axis.

2. The reamer according to claim 1, wherein the outer surface of each flute is curved and said flutes together define a convex outer surface having a diameter larger than the diameter of the inner concave approximately semi-spherical surface formed by rotation of the flutes;

the side cutting surface and said outer surface defining a first edge;

said non-cutting surface and said outer surface defining a second edge; and the angle formed by the intersection of the first edge of a first flute and the adjacent second edge of an adjacent flute is between about 45° and 65°.

3. The reamer according to claim 2, wherein said angle is between about 50° and 60°.

4. The reamer according to claim 3, wherein said angle is about 55°.

5. The reamer according to claim 2, wherein said head and body are cannulated.

6. A kit comprising a plurality of reamers according to claim 2, wherein each of said reamers have flutes with cutting edges upon rotation defining inner semi-spherical surfaces of different diameters and said angle in each said reamer is substantially the same.

7. The kit according to claim 6 wherein a number of said reamers have only three flutes and a number have only five flutes.

8. The device according to claim 1, wherein each flute is identically shaped.

9. The reamer according to claim 1 wherein:

the opposite side non-cutting surface and the inner concave surface form a non-cutting edge; and said inner concave surface of each said flute is slanted such that the diameter of the semi-spherical surface formed by the non-cutting edge of said flutes together upon rotation is larger than the diameter of the semi-spherical surface formed by the cutting edge of said flutes together upon rotation.

10. The reamer according to claim 1 wherein:

the curved cutting edge of each said flute is substantially joined at the first end of said flutes.

11. A reamer for use in creating a convex, curved surface on a bone comprising:

a first portion comprising a cannulated shaft concentric with a central axis;

a second portion at an end of the shaft comprising a cutting head of the reamer, said head comprising at least three substantially equally spaced flutes extending outward from the end of the shaft in a curved manner such that their extending ends are unconnected, each said flute having an outer curved surface, an opposite inner concave surface extending from said shaft to said unconnected end, a side cutting surface, an opposite side non-cutting surface, and an end surface at the extending end of the flute, the curved inner surface and the side cutting surface defining a curved cutting edge that extends radially and longitudinally from the head to the unconnected extending ends of the flutes, the inner surface of said flutes together upon rotation defining a concave substantially semi-spherical surface for creating a convex, curved surface on the end of the bone.

12. The reamer according to claim 11 wherein said side cutting surface and said outer curved surface of a flute define a first edge and said side non-cutting surface and said outer curved surface of the adjacent flute define a second edge, the first edge intersecting the second edge to form a first angle between about 45° and 65°.

13. The reamer according to claim 12 wherein said side cutting surface of each said flute intersects said side non-cutting surface of each said adjacent flute to form an intersection line, the angle between said intersection line and said central axis is between about 35° and 55°.

14. The reamer according to claim 13, including five flutes wherein an angle between the side cutting surfaces of two adjacent flutes is approximately 72°.

15. The reamer according to claim 13, including three flutes wherein an angle formed between the side cutting surfaces of two adjacent flutes is approximately 120°.

16. A reamer for use in creating a curved surface on a bone surface comprising:

a first portion comprising a cannulated shaft concentric with a central axis;

a second portion at an end of the shaft comprising a cutting head of the reamer, said head comprising at least three substantially equally spaced flutes with first and second ends, the first ends connected at the end of the shaft, said flutes extending radially outward and curving longitudinally away from said shaft such that their extended second ends are unconnected, each said flute having an outer curved surface, an opposite inner concave surface extending from the first end to the second end, a side cutting surface, an opposite side non-cutting surface, and an end surface at the second unconnected end, the curved outer surfaces of said flutes together define a substantially convex semi-spherical outer surface.

* * * * *